United States Patent
Nishibayashi

(10) Patent No.: US 8,801,637 B2
(45) Date of Patent: Aug. 12, 2014

(54) BODY MOVEMENT DETECTING APPARATUS AND BODY MOVEMENT DETECTING METHOD

(75) Inventor: Kenji Nishibayashi, Tokyo (JP)

(73) Assignee: Tanita Corporation, Tokyo (JP)

(*) Notice: Subject to any disclaimer, the term of this patent is extended or adjusted under 35 U.S.C. 154(b) by 487 days.

(21) Appl. No.: 12/730,863

(22) Filed: Mar. 24, 2010

(65) Prior Publication Data

US 2010/0256531 A1    Oct. 7, 2010

(30) Foreign Application Priority Data

Apr. 2, 2009    (JP) .................. 2009-090111

(51) Int. Cl.
*A61B 5/103*    (2006.01)

(52) U.S. Cl.
USPC ........................... 600/595; 702/160

(58) Field of Classification Search
USPC ........................... 600/595; 702/160
See application file for complete search history.

(56) References Cited

U.S. PATENT DOCUMENTS

| | | | |
|---|---|---|---|
| 7,653,508 B1 * | 1/2010 | Kahn et al. ............... | 702/160 |
| 2004/0094613 A1 * | 5/2004 | Shiratori et al. .......... | 235/105 |
| 2004/0133081 A1 * | 7/2004 | Teller et al. .............. | 600/300 |
| 2006/0020177 A1 * | 1/2006 | Seo et al. .................. | 600/300 |
| 2008/0214360 A1 | 9/2008 | Stirling et al. | |

FOREIGN PATENT DOCUMENTS

| | | |
|---|---|---|
| EP | 1 302 162 A2 | 4/2003 |
| EP | 1 366 712 A1 | 12/2003 |
| EP | 1 994 883 A1 | 11/2008 |
| JP | 2000-093409 | 4/2000 |
| JP | 2002-191580 | 7/2002 |
| JP | 2003-134027 | 5/2003 |
| JP | 2006-192276 | 7/2006 |
| JP | 2007-097999 | 4/2007 |
| WO | WO 2008/132105 A1 | 11/2008 |

OTHER PUBLICATIONS

European Search Report issued in European Patent Application No. 10156275.9 dated Mar. 22, 2011.
Japanese Office Action issued in Japanese Patent Application No. JP 2009-090111 dated Feb. 4, 2011.

* cited by examiner

*Primary Examiner* — Max Hindenburg
*Assistant Examiner* — Renee Danega
(74) *Attorney, Agent, or Firm* — McDermott Will & Emery LLP

(57) ABSTRACT

There is provided a body movement detecting apparatus having a body movement data acquiring unit configured to detect a body movement of a user and acquire body movement data relating to the body movement and a computing unit configured to calculate consumed energy on the basis of the body movement data, including: a time data acquiring unit configured to acquire time data when the body movement data is acquired; a data accumulating unit being capable of accumulating the body movement data in correspondence with the time data; and a detection condition changing unit being capable of changing a detection condition for detecting the body movement on the basis of the body movement data and the time data accumulated in the data accumulating unit.

11 Claims, 5 Drawing Sheets

BODY MOVEMENT DETECTING APPARATUS AND BODY MOVEMENT DETECTING METHOD

BACKGROUND OF THE INVENTION

1. Field of the Invention

The present invention relates to a body movement detecting apparatus and a body movement detecting method for detecting body movements of a user and calculating energy consumed by the body movements.

2. Description of the Related Art

In the related art, there is a pedometer as one of body movement detecting apparatuses, and more specifically, those added with a calculating function of consumed energy are widely distributed. The pedometer as described above is configured to count the number of steps (step) of the user made by walking (including running, hereinafter), and to calculate consumed energy according to the number of steps. As another body movement detecting apparatus, for example, the one disclosed in JP-A-2002-191580 is proposed. The body movement detecting apparatuses including the pedometer in the related art as described above are configured to perform a process to detect or not to detect the body movements which satisfy preset conditions irrespective of the person who uses the apparatus.

However, the users of the body movement detecting apparatuses diverse as students, workers, homemakers and so on and have different life styles, respectively. Therefore, with the apparatuses which perform the process of detecting the body movement always under certain conditions for all users as the body movement detecting apparatus in the related art, a detection process in which characteristics of the body movement of individual users are taken into consideration cannot be achieved. In contrast, performing the process of detection of the body movement on the basis of detection conditions suitable for the individual users taking how the daily lives of individual users (activity patterns) into consideration achieves further accurate calculation of the consumed energies of the individual users.

In view of such circumstances, it is an object of the present invention to perform a process of detecting a body movement on the basis of detection conditions determined by taking an activity pattern (life pattern, behavior pattern) of an individual user into consideration and hence being suitable for activity patterns of individual users, and calculate consumed energy more accurately according to the detected body movement. In other words, the invention provides a body movement detecting apparatus which is capable of accumulating data relating to the behavior of the individual user continuously, changing the conditions of the body movement detection on the basis of the accumulated data, and calculating the consumed energy according to the body movement detected thereby.

SUMMARY OF THE INVENTION

In order to solve the above-described problem, there is provided a body movement detecting apparatus having a body movement data acquiring unit configured to detect a body movement of a user and acquire body movement data relating to the body movement and a computing unit configured to calculate consumed energy on the basis of the body movement data, including: a time data acquiring unit configured to acquire time data when the body movement data are acquired; a data accumulating unit being capable of accumulating the body movement data in correspondence with the time data; and a detection condition changing unit being capable of changing a detection condition for detecting the body movement on the basis of the body movement data and the time data accumulated in the data accumulating unit.

In the body movement detecting apparatus of the invention, the time data include day of week and time of day when the body movement data are acquired.

The body movement detecting apparatus according to the invention includes an activity pattern data acquiring unit configured to acquire activity pattern data of the user on the basis of the body movement data and the time data accumulated in the data accumulating unit, and the detection condition changing unit is capable of changing the detection condition on the basis of the activity pattern data.

In the body movement detecting apparatus of the invention, the detection condition is a threshold value relating to a body movement strength, and it is possible not to detect the body movement having the body movement strength which does not reach the threshold value by changing the detection condition by the detection condition changing unit.

In the body movement detecting apparatus of the invention, the detection condition is a threshold value relating to determination whether or not the user is walking and/or running, and changing the detection condition by the detection condition changing unit increases the likelihood of determination that the user is walking and/or running in comparison with the state before the change.

In the body movement detecting apparatus of the invention, a change to a power-saving mode is achieved by changing the detection condition by the detection condition changing unit.

In the body movement detecting apparatus of the invention, the body movement data acquiring unit acquires the body movement data at every predetermined unit time, and the detection condition changing unit is capable of changing the detection condition at the every predetermined unit time.

There is provided a body movement detecting method having: a body movement data acquiring step for detecting a body movement of a user and acquiring body movement data relating to the body movement; and an energy computing step for calculating consumed energy on the basis of the body movement data, including a time data acquiring step for acquiring time data when the body movement data is acquired; a data accumulating step being capable of accumulating the body movement data in correspondence with the time data; a detection condition changing step being capable of changing a detection condition for detecting the body movement on the basis of the body movement data and the time data accumulated in the data accumulating unit.

Advantages of the Invention

According to the invention, setting of the body movement detection conditions suitable for the individual user taking the activity pattern of the individual user into consideration is achieved automatically, so that accurate calculation of the consumed energy is achieved according to the body movement detected thereby.

DESCRIPTION OF PREFERRED EMBODIMENT

Figure 1:
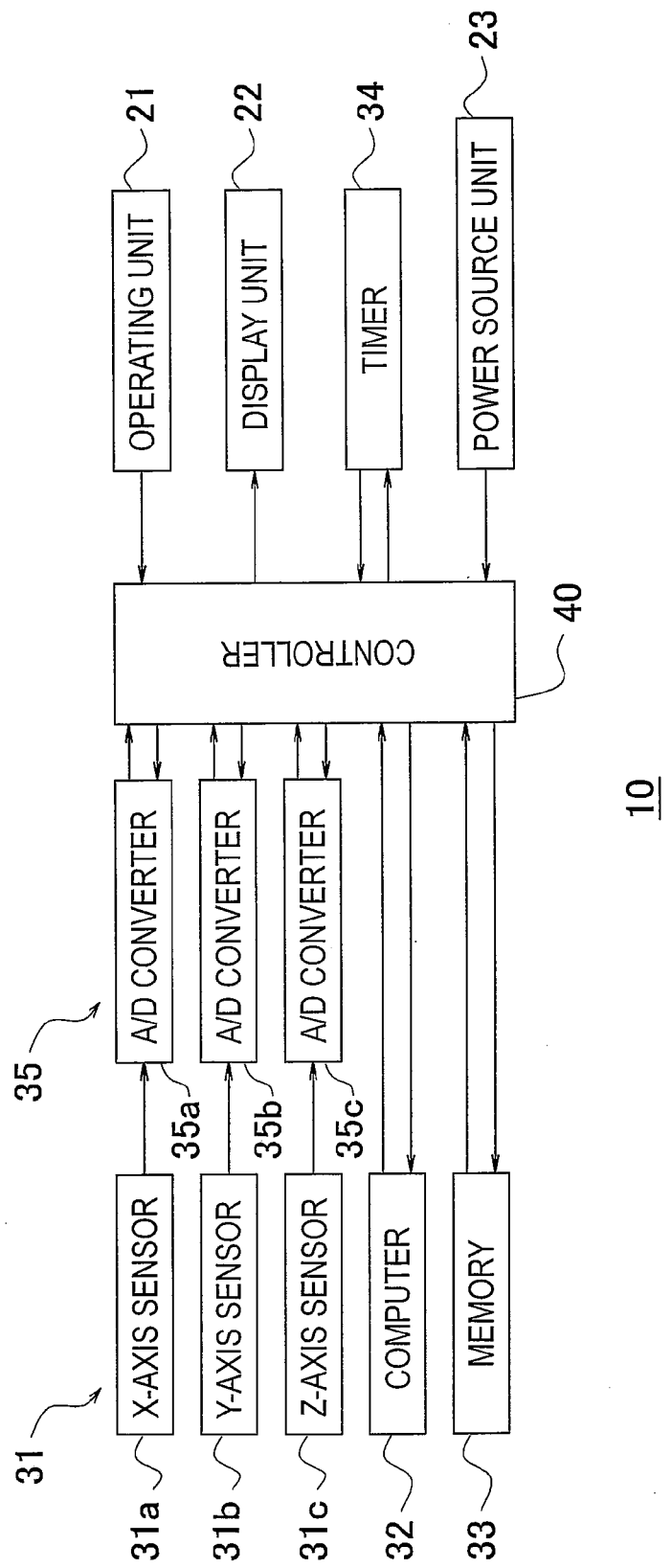
FIG. 1 is a block diagram showing a configuration of a body movement detecting apparatus according to the invention.

Referring now to the drawings, a body movement detecting apparatus according to an embodiment of the invention will be described. FIG. 1 is a block diagram showing a configuration of a body movement detecting apparatus 10. As shown in FIG. 1, the body movement detecting apparatus 10 includes an operating unit 21, a display unit 22, a power source unit 23, an accelerator sensor 31, a computer 32, a memory 33, a timer 34, an A/D converter 35, and a controller 40. Detailed configurations of the respective members will be described below.

In the invention, the term "body movement data" means data on the body movements of a user. More specifically, they are data reflecting the body movements of the user (for example, walking, running, and activities other than those (daily life actions)) such as body movement data relating to the stress of the body movement (body movement strength), repetitiveness and continuity of the body movement, pitches of the body movement when the same body movement is repeated (body movement pitch), the number of times (for example, the number of steps), and includes accumulated body movement data and activity pattern data described later. As the body movement strength, using data relating to acceleration values of the body movement of the user is specifically preferable. The data relating to the acceleration value may be selected as needed from, for example, a value obtained by subtracting a lower peak value from an upper peak value for each body movement, acceleration values themselves for each body movement, or an integrated value of the acceleration values ("magnitudes of the acceleration values") per a given period.

The body movement includes general actions of the body of the user, and includes walking, running, and, in addition, other activities (for example, a step action without or little repetitiveness or continuity, an action only of the upper half body, mainly, daily life actions).

The operating unit 21 (biological data acquiring unit) functions mainly as a data input unit for inputting the biological data of the user or inputting setting items of the body movement detecting apparatus 10. The number, the shape, and the operating method of the operating unit 21 are not specifically limited, and may be selected as needed from, for example, those of a push-button type, a touch sensor type, and a dial type. Here, as the biological data to be input by the operating unit 21, weight, height, age, sex, and lean body mass may be exemplified for example. However, the biological data are not specifically limited as long as they are needed for obtaining consumed energy by the body movement of the user as described later. The setting items are setting items required when the user uses the body movement detecting apparatus 10, and initial settings of the body movement detecting apparatus 10, the day of week and time of day of the present, change-over of contents to be displayed on the display unit 22 are exemplified for example. The biological data and the setting items input in this manner are memorized in the memory 33 (for example, RAM (Random Access Memory) under control of the controller 40, and are displayed on the display unit 22.

The display unit 22 is a data display unit for displaying data transmitted from the controller 40, and mainly displays the biological data and the setting items of the user, an operation guide, current time of day, date, day of week, accumulated consumed energy, number of steps, walk distance, time length of activities other than the walking, and resting time length of the corresponding day, and data of past several days. The contents to be displayed are memorized in the memory 33, and the controller 40 is configured to read out data from the memory 33 according to the state of usage of the body movement detecting apparatus 10 according to a program memorized in the memory 33 in advance, and displays on the display unit 22. For example, a display unit employing an LCD (Liquid Crystal Display) may be used as the display unit 22, and the display unit 22 and the operating unit 21 may be formed integrally as a liquid crystal display panel having, for example, a touch panel function.

The power source unit 23 is a power supply unit made up of a power supply source such as a battery, so that power is supplied to the respective components of the body movement detecting apparatus 10 via the controller 40.

The body movement detecting apparatus 10 includes the accelerator sensor 31, the computer 32, the memory 33, the timer 34, the A/D converter 35, and the controller 40 as an internal mechanism. The computer 32 and the controller 40 each are preferably formed integrally by an integrated circuit.

The memory 33 is a memory unit made up of a volatile memory (not shown), or a non-volatile memory (not shown). The volatile memory is configured to be able to memorize a variety of data for the processes by the controller 40 temporarily. It also functions as the memory area used by the computer 32 for a computing process. The non-volatile memory is used for storing data to be memorized for a long term. For example, the non-volatile memory is configured to be used for storing past body movement data (including determination values) on the basis of day of week and time of day, biological data input by the user, consumed energy calculation formulas, and a variety of programs as described later.

The timer 34 measures elapse of predetermined time and determines whether or not the predetermined time is elapsed and, for example, is able to measure the elapsed time from a moment when the user starts to use the body movement detecting apparatus 10, or to determine body movement pitches of the user (for example, time required for one step). In the embodiment, the timer 34 is an independent component. However, it may be integrated into the controller 40 as a timer circuit to determine whether the predetermined time is elapsed or not by the controller 40 by itself. The timer 34 also acquires time data when the user's body movement data are acquired under control of the controller 40 as a time data acquiring unit. The acquired time data are memorized in a predetermined area in the memory 33 together with the corresponding body movement data. Here, the time data includes, for example, day of week, data, time of day, and time zone. The time data may be used as a time axis (reference time) of the activity pattern of the user.

The accelerator sensor 31 is a body movement data acquiring unit configured to acquire the body movement data relating to the body movement of the user, and is a sensor which outputs values varying according to the acceleration values generated by the body movement of the user. More specifically, the accelerator sensor 31 includes an X-axis sensor 31a, a Y-axis sensor 31b, and a Z-axis sensor 31c (see FIG. 1), so as to be capable of detecting the body movement in the 3-axis (X-axis, Y-axis, Z-axis) directions orthogonal to each other, and is configured to be able to acquire acceleration values, which is a value obtained by combining respective output values from the X-axis sensor 31a, the Y-axis sensor 31b, and the Z-axis sensor 31c. In the embodiment, the accelerator sensor 31 is used as the body movement data acquiring unit, and hence the body movement strength of the user corresponds to the data relating to the acceleration values. Therefore, the body movement data is obtained in such a manner that the body movement strength is determined to be strong if the acceleration value is high, and the body movement strength is determined to be weak if the acceleration value is low.

The output acquired by the accelerator sensor 31 is converted from analogue to digital by the A/D converter 35 for the processes performed by the controller 40 or the computer 32. More specifically, the respective output values as analogue data acquired by the X-axis sensor 31a, the Y-axis sensor 31b, and the Z-axis sensor 31c are converted into digital data respectively by an A/D converter 35a, an A/D converter 35b, and an A/D converter 35c, and are memorized in the memory 33 corresponding to the time data such as the day of week and the current time of day (time zone) of the day of acquisition, or the elapsed time from the start of acquisition in conjunction with the timer 34. Also, by combining the A/D converted values of the respective output values from the X-axis sensor 31a, the Y-axis sensor 31b, and the Z-axis sensor 31c by the computer 32, acceleration values (the A/D converted value of the acceleration values) as digital data are obtained by calculation, and is memorized in the memory 33 in correspondence with the time data in conjunction with the timer 34. In this manner, by acquiring the acceleration values corresponding to the time data, not only the body movement strength, but also the presence or absence of the repetitiveness or continuity of the body movement, the pitch (body movement pitch) or the number of times (for example, the number of steps) when the same body movement is repeated may be acquired simultaneously as the body movement data by observing the acceleration value in time series in sequence of acquisition. In order to acquire the acceleration values by all the body movements of the user accurately by this accelerator sensor 31, the body movement detecting apparatus 10 is preferably mounted to the user so as to be in contact thereto as close as possible and, it is recommended to propose a state of being attached, for example, on a belt or the like worn by the user around the waist, or a state of being memorized in a chest pocket of a dressing of the user specifically for enabling sensing of the body movement of the upper half body as well. The body movement data acquired in this manner is memorized in the memory 33 and is partly (for example, the number of steps) displayed on the display unit 22 by the control of the controller 40.

As shown in FIG. 1, the controller 40 is electrically connected to the operating unit 21, the display unit 22, the power source unit 23, the accelerator sensor 31, the computer 32, the memory 33, the timer 34, and the A/D converter 35 so that the respective operations are controlled by the controller 40.

The controller 40 functions as a detection condition changing unit configured to change the detection conditions (threshold values) of the body movement on the basis of the body movement data accumulated already together with the time data. As the detection conditions to be changed, for example, a threshold value relating to the determination whether or not the user is in activity (predetermined threshold values of the acceleration values (body movement strengths)), or a threshold values relating to the determination whether or not the user is walking (predetermined threshold values of coefficient of variance) is exemplified.

The controller 40 functions as a data accumulating unit which is able to accumulate the body movement data continuously corresponding to the time data (day of week, time of day (time zone)) together with the memory 33. Accordingly, after having started the utilization of the body movement detecting apparatus 10, the activity pattern data of the individual user who uses the body movement detecting apparatus 10 can be acquired, and the controller 40 functions as an activity pattern data acquiring unit.

More specifically, whether the body movement data acquired by the accelerator sensor 31 at every predetermine unit time (the body movement data acquired immediately before) are from the state of walking, from the resting state, or from the state other than those (daily life actions) are determined, and are accumulated on the basis of the day of week, or on the basis of time (time of day, time zone). By accumulating the body movement data as described above continuously with the time data, the data relating to the activity pattern of the individual user, that is, the activity pattern data can be obtained. The activity pattern data is data on the basis of the body movement data and the time data. Specifically, they are data of the activity which is often taken by the individual user patterned corresponding to the time data and, for example, the activity pattern data such that the frequency of walking is high at 8 o'clock in the morning on Monday, the frequency of being rest is high at 8 o'clock in the morning on Sunday, and the rhythm of the life is obviously different between weekdays from Monday to Friday and weekends, that is, Saturday and Sunday can be exemplified. Detailed description will be given later.

Furthermore, the controller 40 also functions as a comparing unit which is configured to compare whether or not the body movement data acquired at the instance just passed by the accelerator sensor 31 correspond to the body movement data of the user in the past which are already accumulated (accumulated body movement data). More specifically, the controller 40 compares determination values of the body movement data acquired individually at every predetermined unit time with the accumulated body movement data. Here, the determination values are not specifically limited as long as they are able to reflect the characteristics of the body movement data, and a detailed example will be described later.

The controller 40 further functions as a number-of-steps counting unit. An example of a number-of-steps counting method performed by the controller 40 will be described in brief below. The controller 40 causes the A/D converter 35 to convert the acceleration values acquired by the accelerator sensor 31 from analogue to digital and causes the memory 33 to memorize the acquired digital acceleration values in sequence in time series and, for example, acquires a waveform by plotting all the A/D converted values of acceleration values acquired in sequence with a lateral axis indicating the elapsed time (unit: second) and a vertical axis indicating the A/D converted value of the acceleration value (unit: count), and then performs the following process according to the transition of the acceleration value. The amplitude of the waveform of the acceleration value is determined as one step of walking (when the value exceeds a first threshold value X and is acquired within a given period t1), whether a predetermined number of such waves or larger appear within the predetermined time (whether or not the number of waves in the waveform of the acceleration value within a given period t2 exceeds a second threshold value Y) is determined. If the number of the waves is the predetermined number of waves or larger, it is determined to be a continuous walking, so that the steps are counted by incrementing by one at every peak value.

The computer 32 is a computing unit being capable of performing a variety of computing processes under control of the controller 40 and, for example, calculates consumed energy by the body movement of the user on the basis of the biological data or the body movement data of the user memorized in the memory 33. Calculation of the consumed energy is performed by cumulatively adding the consumed energy of the body movement data (body movement data at the instance just passed) at every predetermined unit time (for example 20 seconds).

A detailed method relating to the calculation of the consumed energy is not specifically limited. However, in the embodiment, it is performed as follows. When the controller 40 as a body movement determining unit determines that the body movement data at every predetermined unit time is walking, the computer 32 calculates the consumed energy on the basis of a "consumed energy calculation formula for walking" using the body movement pitch, the number of steps, and so on as parameters. In contrast, when the controller 40 determines that the body movement data at every predetermined unit time are activities other than the walking, the computer 32 calculates the consumed energy on the basis of a "consumed energy calculation formula for activities other than the walking" using the body movement strength as a parameter. By cumulatively adding the consumed energy at the predetermined unit time calculated in this manner, for example, the total consumed energy of the corresponding day of usage is calculated.

The consumed energy calculation formula for walking is, for example, "weight of user×number of steps×coefficient". The coefficients may be set arbitrarily as constant values determined according to the body movement pitches multiplied by coefficients determined according to the body movement strengths. As the constant values determined by the body movement pitches, for example, when the time required for one step (body movement pitch) falls within a range from 250 ms inclusive to 300 ms exclusive, the coefficient to be set is $c_1$, when it falls within a range from 300 ms inclusive to 350 ms exclusive, the coefficient to be set is $c_2$. In this manner, the coefficients which increment by time 50 ms in sequence (for example, $c_1 < c_2 < \ldots$) may be set. In contrast, the coefficients determined according to the body movement strengths may be, for example, coefficients determined according to data relating to the measured acceleration value, which are obtained by classifying the "magnitude of the acceleration value" into arbitrary steps and setting the same from a state in which the "magnitude of the acceleration value" is small toward a state in which the "magnitude of the acceleration value" is large in sequence (for example, $a_1 < a_2 < \ldots$).

In contrast, the calculation formula for calculating the consumed energy during the activities other than the walking is, for example, "weight of user×magnitude of acceleration value×first coefficient+second coefficient". Here, the first coefficient and the second coefficient may be determined arbitrarily, but it is preferable to set different values according to the sex (biological data). When the height and the lean body mass can be used in addition to the sex as the biological data of the user, further accurate consumed energy may be calculated by introducing terms including these items. In this case, it is preferable to prepare the calculation formulas separately according to the sex.

Figure 2:
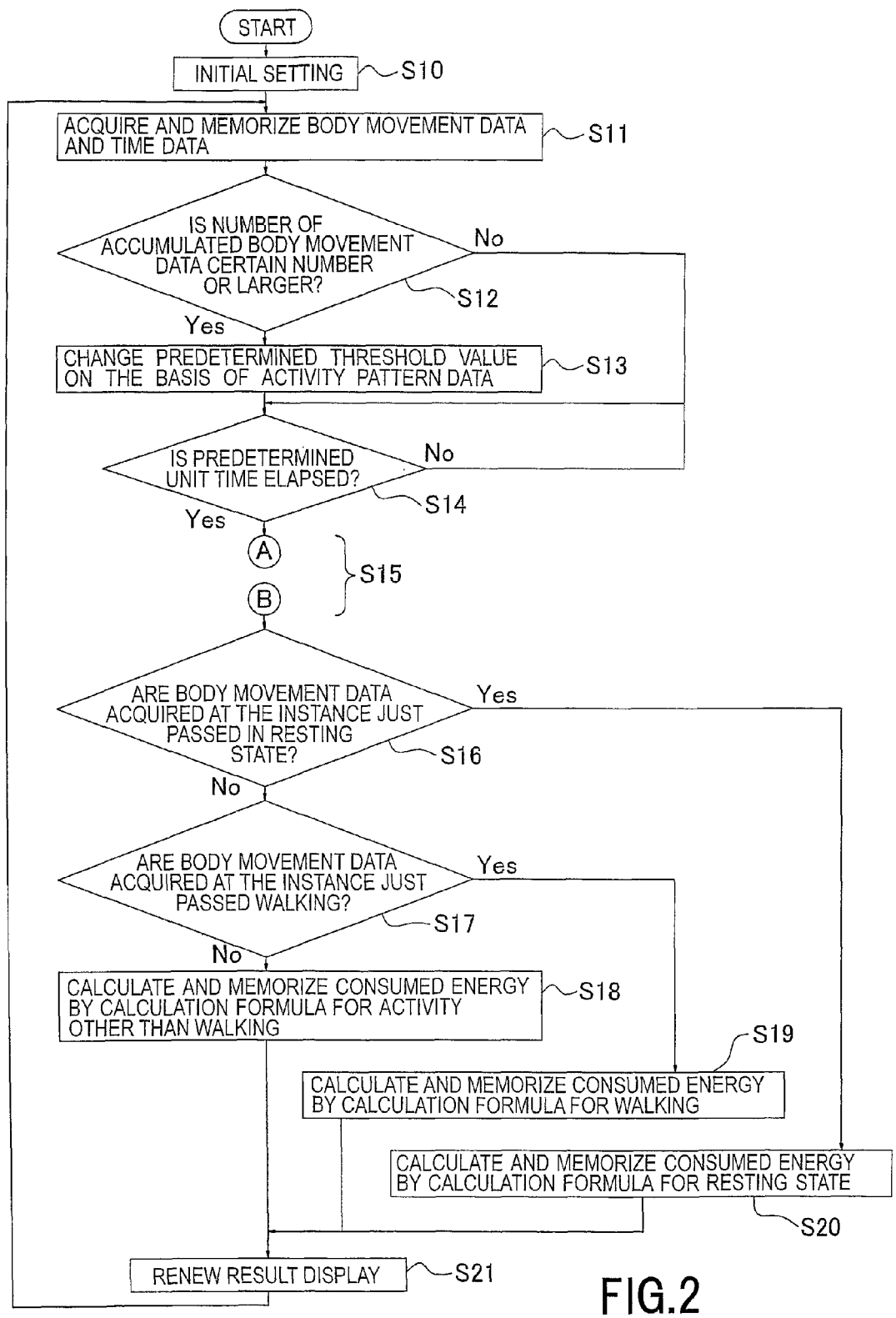
FIG. 2 is a flowchart showing an example of a flow of an operation of the body movement detecting apparatus according to the invention.
Figure 3:
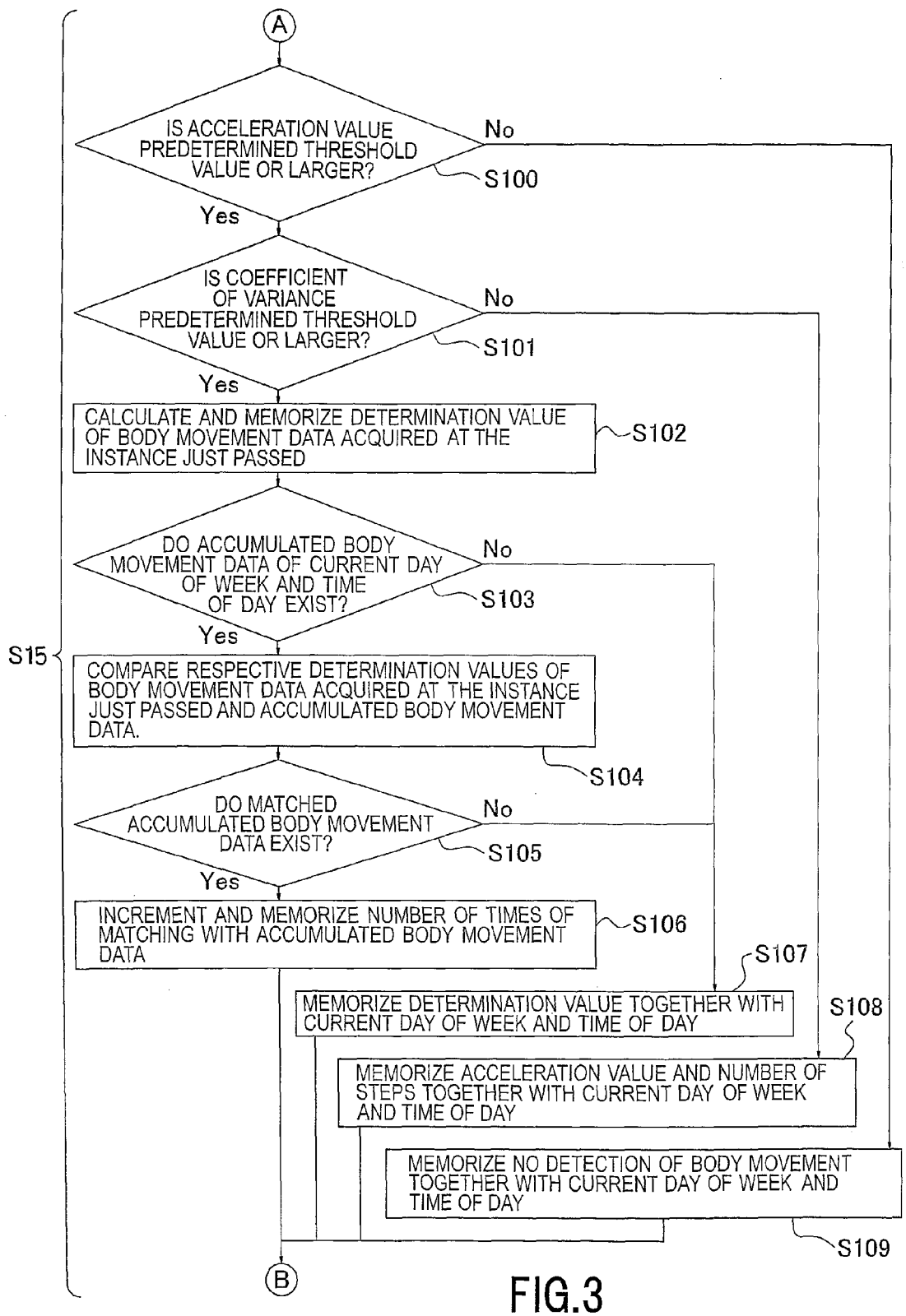
FIG. 3 is a flowchart showing a data accumulating process of the body movement detecting apparatus according to the invention.
Figure 4:
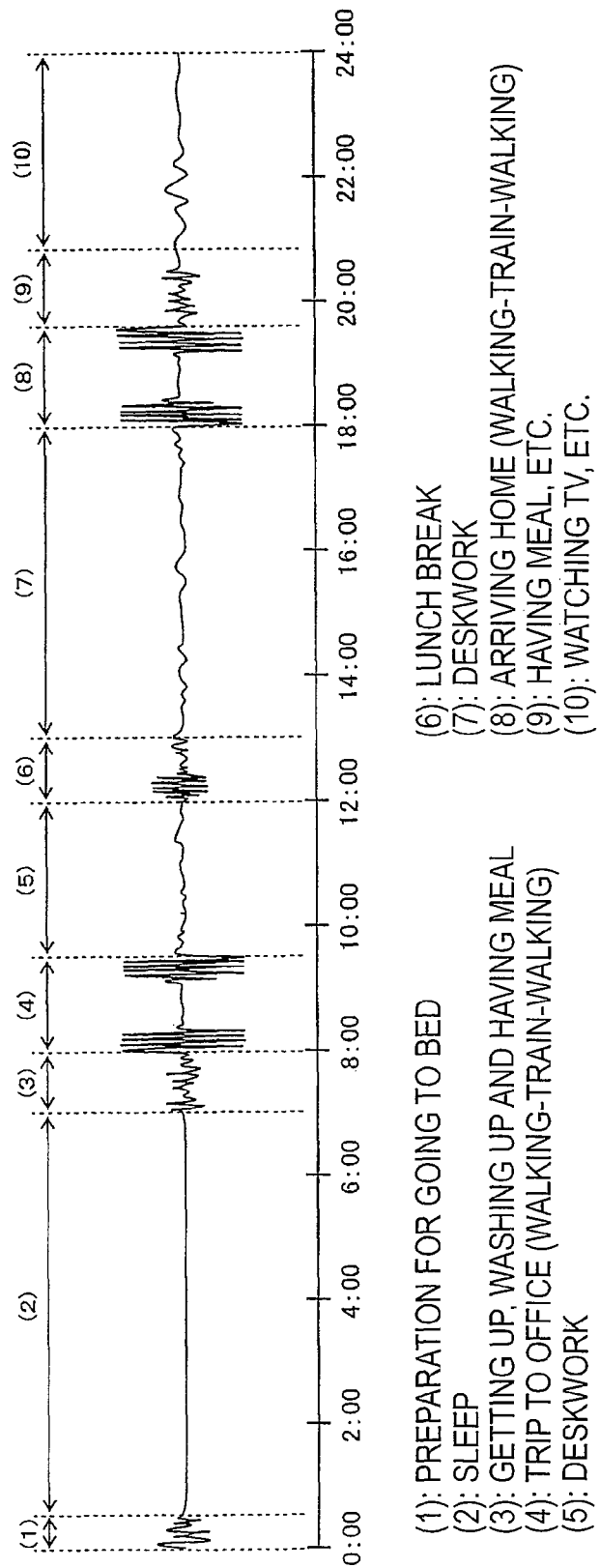
FIG. 4 is a drawing showing an example of an activity pattern of weekdays of a user of the body movement detecting apparatus according to the invention.
Figure 5:
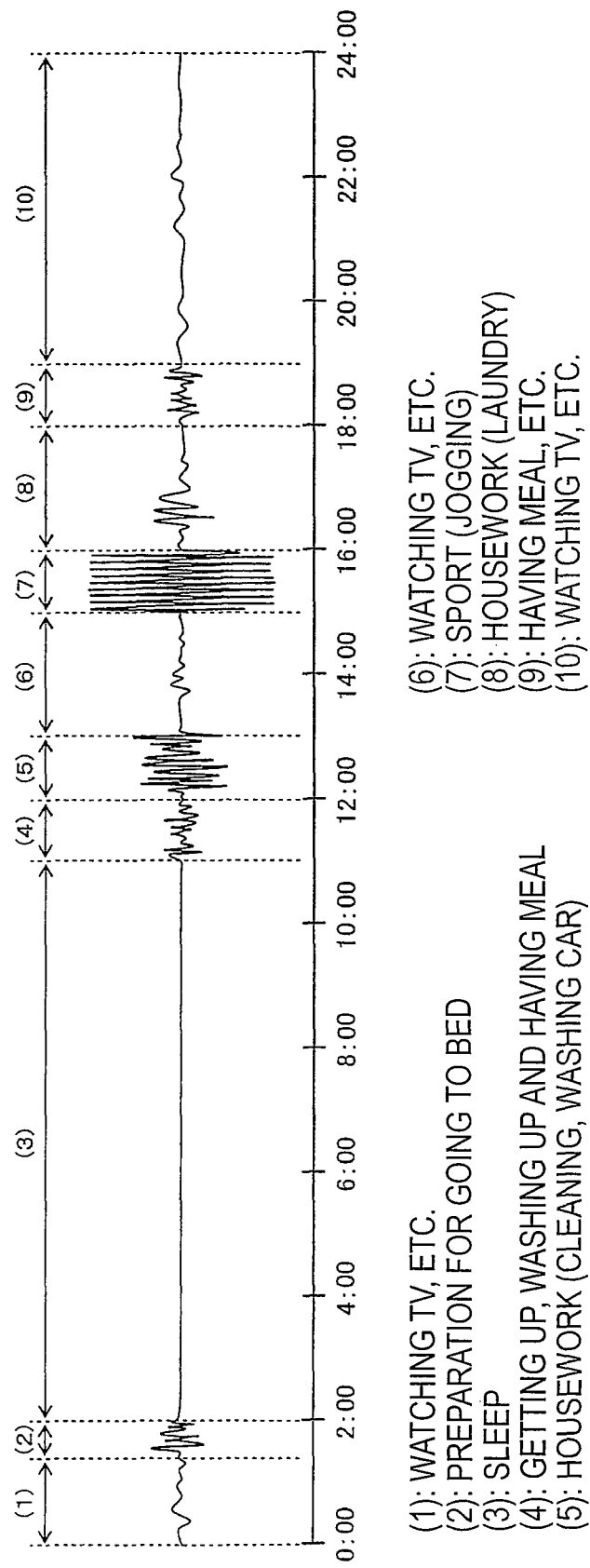
FIG. 5 is a drawing showing an example of an activity pattern in holidays of the user of the body movement detecting apparatus according to the invention.

Referring now to FIG. 2 to FIG. 5, a body movement detecting method using the body movement detecting apparatus 10 will be described. FIG. 2 is a flow chart showing an example of a flow of operation of the body movement detecting apparatus according to the invention. FIG. 3 is a flowchart showing a data accumulating process of the body movement detecting apparatus according to the invention. FIG. 4 is a drawing showing an example of an activity pattern in weekdays of the user of the body movement detecting apparatus according to the invention. FIG. 5 is a drawing showing an example of an activity pattern in holidays of the user of the body movement detecting apparatus according to the invention.

After having activated the body movement detecting apparatus 10, the user operates the operating unit 21, inputs biological data required mainly for calculating the consumed energy (for example, weight, sex, height, lean body mass, etc.), performs an initial setting such as setting of the current day of week and time of day, and memorizes the input biological data and the setting items in a predetermined area of the memory 33 (Step S10). After having ended this initial setting, the user attaches the body movement detecting apparatus 10 at a predetermined position such as a dressing of the user.

Subsequently, the body movement detecting apparatus 10 acquires the body movement data and the time data of the user, and memorizes the same in the memory 33 (Step S11, body movement data acquiring step, time data acquiring step). More specifically, the acceleration values of the body movement of the user are acquired by the accelerator sensor 31, then, the A/D converter 35 converts the respective output values acquired by the X-axis sensor 31a, the Y-axis sensor 31b, and the Z-axis sensor 31c of the accelerator sensor 31 from analogue to digital. The controller 40 acquires elapsed time from a time point when the acquisition is started by the timer 34 and time data such as the current day of week and the current time of day simultaneously, and memorizes the A/D converted values of the respective output values in the memory 33 in correspondence with the time data (body movement data acquiring step, time data acquiring step).

Subsequently, the controller 40 determines whether or not the number of the accumulated body movement data at the time of day corresponding to the current time of day in the day of week which is the same as the current day of week is a certain number or larger (Step S12). For example, when the day and time when the acquisition of the body movement data is started in Step S11 is 7:00 a.m. on Monday, whether or not there are a certain number of the accumulated body movement data or larger acquired and accumulated from 7:00 a.m. on past Monday for a predetermined unit time (see Step S14) is determined (Step S12). Therefore, since the number of accumulated body movement data is zero if at least one week is not elapsed from the start of usage, so that the determination in Step S12 is No. The number of the accumulated body movement data to go Yes in Step S12 is arbitrary as long as it is the number suitable for grasping the activity pattern of the user.

Since an initial period of usage of the body movement detecting apparatus 10, the number of the accumulated body movement data does not reach the certain number (No in Step S12), and hence the activity pattern of the user cannot be grasped yet. Therefore, the acquisition and the memorization of the body movement data are continued with the default setting as regards the detection conditions (threshold values) of the body movement (do not pass through Step S13). Whether or not a predetermined unit time (for example, 20 seconds) is elapsed from the start of the acquisition of the body movement data is counted by the timer 34 (Step S14). If it is not elapsed (No in Step S14), the acquisition and the memorization of the body movement data are continued without any change, and observation of the elapse of the predetermined unit time is continued.

In contrast, when at least several weeks are elapsed from the start of usage of the body movement detecting apparatus 10 and the number of the accumulated body movement data reaches the certain number or larger (Yes in Step S12), the activity pattern of the user can be grasped. Therefore, in order to perform the process of detection of the body movement on the basis of the detection conditions suitable for the individual user that actually uses the body movement detecting apparatus, the controller 40 performs a detection condition changing process for changing the detection conditions (predetermined threshold values) of the body movement on the basis of the accumulated body movement data (Step S13, detection condition changing step). The change of the detection conditions is adapted to be performed at every predetermined unit time (20 seconds in the embodiment), whereby the detection conditions of the body movement of the user can be changed frequently. The detection condition changing process is described further in detail below.

As a premise of the detection condition changing process, description will be started from the data accumulating process. As described above, the acquisition of the body movement data by the body movement detecting apparatus 10 is performed at every predetermined unit time (see Step S14 in FIG. 2). Therefore, by connecting the body movement data (acceleration values in the embodiment) acquired at the every predetermined unit time by an amount corresponding to one day (24 hours), the activity pattern of the user for one day can be observed (see FIG. 4 and FIG. 5). Here, the activity pattern of a certain user for one day and the variations in acceleration value thereby are shown in FIG. 4 and FIG. 5 in a simplified manner. FIG. 4 is an example of an activity pattern in weekdays in a case where the user is a sedentary office worker.

time zone (1) [0:00 to 0:30]: Preparation for going to bed. Irregular acceleration values are acquired due to the activities such as washing up.
    time zone (2) [0:30 to 7:00]: Sleep. Since the body movement detecting apparatus 10 is placed nearby, and hence the acceleration values are not detected.
    time zone (3) [7:00 to 8:00]: Irregular acceleration values are detected due to the activities such as getting up, washing up, and having a meal.
    time zone (4) [8:00 to 9:30]: Trip to Office. Regular and large acceleration values are detected due to walking from home to the station, then irregular small acceleration values are detected due to fine vibrations while being in the train, then regular and large acceleration values are detected due to walking from the station to the company.
    time zone (5) [9:30 to 12:00]: Desk work. Irregular acceleration values are detected due to the behaviors such as sitting, standing up, and walking near his/her own desk.
    time zone (6) [12:00 to 13:00]: Lunch Break. Irregular acceleration values are detected due to the behaviors such as having a meal.
    time zone (7) [13:00 to 18:00]: Deskwork. Irregular acceleration values are detected due to the behaviors such as sitting, standing up, and walking near his/her own desk.
    time zone (8) [18:00 to 19:30]: Leaving Office to Arriving Home. Substantially the same as the time zone (4).
    time zone (9) [19:30 to 21:00]: Irregular acceleration values are detected due to the behaviors such as having a meal and taking a bath, etc.
    time zone (10) [21:00 to 24:00]: Irregular acceleration values are detected due to the behaviors such as spending time in a living room by watching TV etc.

The activity pattern in weekdays shown in FIG. 4 is an example only, but if the user is the sedentary office worker, it can be said generally that he or she spends a day in a life style as described above in relatively many cases as regards the weekdays (for example, from Monday to Friday). In particular, the user takes actions in the same manner everyday as regards the time zone (3) and the time zone (4) until he or she arrives the office, such as getting up at a regular time, leaving home at a regular time, and getting on the train which leaves at a regular time. It is not limited to the office workers, but in a case where the user is a student or a homemaker as well, he or she spends a day in the same life style during the weekdays (for example, from Monday to Friday) in relatively many cases.

In contrast, FIG. 5 shows an example of the activity pattern in holidays of the user shown in FIG. 4.

time zone (1) [0:00 to 1:30]: Irregular acceleration values are detected due to the behaviors such as spending time in a living room by watching TV etc.
    time zone (2) [1:30 to 2:00] Preparing for going to bed. Irregular acceleration values are acquired due to the behaviors such as washing up.
    time zone (3) [2:00 to 11:00]: Sleep. Since the body movement detecting apparatus 10 is placed nearby, and hence the acceleration values are not detected.
    time zone (4) [11:00 to 12:00]: Irregular acceleration values are detected due to the behaviors such as getting up, washing up, and having a meal.
    time zone (5) [12:00 to 13:00]: Irregular acceleration values are detected due to housework such as cleaning or washing car.
    time zone (6) [13:00 to 15:00]: Irregular acceleration values are detected due to the behaviors such as spending time in a living room by watching TV etc.
    time zone (7) [15:00 to 16:00]: Sport. For example, in a case of jogging, regular and large acceleration values are detected.
    time zone (8) [16:00 to 18:00]: Irregular acceleration values are detected due to housework such as laundry.
    time zone (9) [18:00 to 19:00]: Irregular acceleration values are detected due to the behaviors such as having a meal and taking a bath, etc.
    time zone (10) [19:00 to 24:00]: Irregular acceleration values are detected due to the behaviors such as spending time in a living room by watching TV etc.

The activity pattern in weekdays shown in FIG. 5 is only an example as in FIG. 4, but it is determined that a transition of the acceleration value which is completely different from the transition of the acceleration value of a day (see FIG. 4) acquired on weekdays (for example, from Monday to Friday) is obtained. It can be said that the activity patterns in holidays such as Saturday or Sunday demonstrate larger variations of data relating to the activity than the case of the weekday because the user may spend time at home whole day, or may go out from the morning and enjoy leisure activity.

In this manner, the body movement data of the user are acquired by the body movement detecting apparatus 10 continuously for more than several weeks, and are accumulated in correspondence with the current day of week and time of day. The controller 40 is capable of acquiring the activity pattern data such as the type of the activity and the frequency thereof taken by the user on respective days of week and respective times of day taking the accumulated body movement data accumulated in this manner into consideration. For example, when the body movement data are acquired at 9 o'clock on Monday, it allows an estimate such that this user takes the same behavior (getting on the train) which demonstrates the highest frequency from among the accumulated body movement data relating to 9 o'clock on Monday. For example, the transition of the acceleration value in one day on Saturday and Sunday every week is completely different from the transition of the acceleration value in one day from Monday to Friday every week (see FIG. 4), it allows an estimate such that this user's holidays are Saturday and Sunday. In this manner, the acquisition of the activity pattern data of the user is achieved. Therefore, the body movement detecting apparatus 10 allows to change the detection conditions of the body movement which match the individual user or to change the mode between the weekday mode and the holiday mode automatically without being operated by the user.

Subsequently, the content of the detection condition changing process in Step S13 in FIG. 2 will be described. First of all, as the detection conditions for detecting the body movement of the user, for example, (1) a threshold value relating to the acceleration value (body movement strength) which determines that the user is in activity when the acceleration value is the threshold value or larger (see Step S100 in FIG. 3, described later), and (2) a threshold value relating to the coefficient of variance which determines that the user is walking when the coefficient of variance is smaller than the threshold value (Step S101 in FIG. 3 described later) may be exemplified.

The body movement data (acceleration value) acquired at the instance just passed is the threshold value or larger described in (1) above, it is determined that the user takes some activity and the consumed energy is calculated. However, this threshold value may be preferable to be processed by determining that the user is not in activity by heightening the threshold value in predetermined cases.

For example, in a case where the user is on the train, the bus, or the car, the mechanical vibrations generated when the train or the like is traveling are detected by the accelerator sensor 31 of the body movement detecting apparatus 10. Consequently, the body movement detecting apparatus 10 calculates the consumed energy corresponding thereto by determining the vibrations to be the activity of the user him/herself. However, since the user him/herself is only standing or sitting in fact, the consumed energy taking the vibrations into consideration becomes noise.

Therefore, in such a case, it is recommended to perform a change to heighten the threshold value relating to the acceleration value so that the acceleration value due to the mechanical vibrations generated when the train or the like is traveling is not determined as the activity of the user him/herself. However, the threshold value relating to the acceleration value is changed only when it is estimated to be noise from the behavior of the user in ordinary times.

In contrast, when observing the transition of the acceleration value while the user is walking, an amplitude at pitches corresponding to the respective steps is confirmed. Therefore, in the default setting, it is determined that the user is walking when the body movement data acquired at the instance just passed, for example, the steps having a predetermined amplitude at a predetermined pitch are confirmed within a predetermined time, that is, when they are stable and regular without variations such that the coefficient of variance is the predetermined threshold value or smaller, so that the number of steps is counted. The coefficient of variance is a value obtained by dividing a standard deviation by an average value.

However, for example, there is a case where the user walks with irregularly instead of continuously such as walking around his/her own desk little and returning back to the desk during the deskwork. In this case, with the default setting as described above, such the case causes the coefficient of variance to be the threshold value or larger and hence is not determined to be walking, so that the number of steps in this case is not counted.

Therefore, in order to obtain the number of steps that the user walks and the walk distance on the number of steps as accurate as possible as values, it is preferable to perform a change to heighten the threshold value relating to the coefficient of variance to increase the likelihood of being determined as the walking in comparison with the default setting. However, it is recommended to change the threshold value relating to the coefficient of variance only when it may be determined as the walking.

The case where the body movement detection conditions (threshold values) as described above are to be changed (Step S13 in FIG. 2) is determined individually on the user-to-user basis in detail on the basis of the body movement data accumulated with the time data. More specifically, it is achieved by acquiring the activity pattern data of the individual user who uses the apparatus actually on the basis of the body movement data memorized together with the time data in advance, and taking the acquired data into consideration.

The acquisition of the activity pattern data will be described. For example, it is determined that days from Monday to Friday are weekdays and Saturday and Sunday are holidays as a result of analysis of the accumulated body movement data. Also, it is determined that if the frequency of detection of the predetermined small irregular acceleration values is the highest at 9 o'clock (and/or this time zone) of weekday, it allows an estimate such that it is caused by vibrations of transport facilities (train or the like) that the user uses to go to office (see the time zone (4) in FIG. 4). Therefore, activity pattern data such that the frequency that the user takes the activity pattern using the transport facilities (train or the like) is high at 9 o'clock of weekdays are acquired. In the same manner, when the predetermined acceleration value is detected in the time zone from 13:00 to 17:00 from Monday to Friday, it allows an estimate such that the user is doing the deskwork in the place of work (see time zone (7) in FIG. 4). Therefore, activity pattern data such that the frequency of taking the activity pattern that the user is at the deskwork in the place of work is high at 14 o'clock of weekdays are acquired.

In this manner, since a certain number of the accumulated body movement data or larger at every day of week and every time of day are accumulated, the controller 40 performs the similar analysis to those described above continuously with the computer 32, acquires and renews the activity pattern data of the user that actually uses the apparatus in each day of week and each time of day, and memorizes the renewed data in the memory 33. The activity pattern data on the same week of day and the same time of day are not limited to one, and a plurality of the activity pattern data may be acquired according to the frequency of the activity pattern.

Considering the activity pattern data acquired in this manner, the detection conditions of the body movement (threshold values) are changed. In other words, for example, the body movement detecting apparatus 10 makes determination in such a manner that when acquisition of body movement data is started at 9 o'clock on Monday (Step S11), the user would be in activity relating to the activity pattern data of the highest frequency at 9 o'clock on Monday (utilization of the transport facilities in the example described above), and performs a change to heighten the threshold value relating to the acceleration value for the acquisition of the body movement data at that time (Step S13). Considering the activity pattern data indicating that Monday is highly likely a weekday for this user, the change as described above may be performed as the weekday mode. In contrast, when the current day of week is Saturday or Sunday, considering the activity pattern data indicating that Saturday and Sunday are highly likely holidays for this user, the change as described above may not be performed as in the holiday mode.

Also, the body movement detecting apparatus 10 makes determination in such a manner that when acquisition of body movement data is started for example at 14 o'clock on Monday (Step S11), the user would be in activity relating to the activity pattern data of the highest frequency at 14 o'clock on Monday (deskwork in the example described above), and performs a change to heighten the threshold value relating to the coefficient of variance for the acquisition of the body movement data at that time (Step S13).

As another example of changing the body movement detection conditions will be given below. As regards a certain time zone when the body movement of the user cannot be detected in many cases as the time zone (2) in FIG. 4 and the time zone (3) in FIG. 5, an estimate such that the user is sleeping is possible. Therefore, the activity pattern data such that the frequency of taking the activity pattern being in sleep is high in the time zone (2) in FIG. 4 and the time zone (3) in FIG. 5 are acquired. Then, the controller 40 of the body movement detecting apparatus 10 may switch the mode to the power-saving mode according to the time zone (2) in FIG. 4 and the time zone (3) in FIG. 5. It is preferable to adapt the time zone to be changed automatically between the case of the weekday mode and the case of the holiday mode. The content of the power-saving mode is not specifically limited as long as it reduces the power to be consumed by the body movement detecting apparatus 10 as a whole such as a release of energization of the display unit 22 or a change of the detection conditions of the accelerator sensor 31. Accordingly, when a battery is used as the power source unit 23 in particular, the power consumption is restrained, and hence the up-time of the battery can be elongated.

Subsequently, referring to FIG. 2 and FIG. 3, the body movement detecting method using the body movement detecting apparatus 10 will be described. When a predetermined unit time is elapsed from the start of acquisition of the body movement data (Yes in Step S14), the data accumulating process for accumulating the body movement data acquired during the predetermined unit time (the body movement data acquired at the instance just passed) as the accumulated body movement data (Step S15) is performed. In this data accumulating process, the process of accumulating the newest body movement data acquired in sequence at every predetermined unit time is performed from content to content (walking or activities other than walking, etc.), for each of current day of week and time of day, which will be described with reference to FIG. 3. As steps from A to B in FIG. 2, steps from A to B in FIG. 3 are executed.

The controller 40 determines whether or not the acceleration value of the body movement data acquired at the instance just passed is the predetermined threshold value or larger (Step S100). As described before, the predetermined threshold value is a threshold value relating to the acceleration value which determines that the user is in activity when the acceleration value is the threshold value or larger, and an arbitrary value is set as a default value. When the threshold value is changed in the Step S13 described above, the determination is performed using the threshold value after the change. When the acceleration value of the body movement data acquired at the instance just passed does not reach the predetermined threshold value (No in Step S100), the controller 40 determines that the user is not moving, and memorizes the fact that the body movement is not detected in the memory 33 together with the current day of week and time of day as the accumulated body movement data (Step S109). Therefore, a case where the body movement detecting apparatus 10 is placed nearby such as the time zone (2) in FIG. 4 or at the time of sleeping in the time zone (3) in FIG. 5.

On the other hand, when the acceleration value of the body movement data acquired at the instance just passed is the predetermined threshold value or larger (Yes in Step S100), the controller 40 determines whether or not the coefficient of variance of the body movement data acquired at the instance just passed is the predetermined threshold value or larger (Step S101). As described before, the predetermined threshold value is a threshold value relating to the coefficient of variance which determines that the user is walking (including running) when the coefficient of variance is smaller than the threshold value, and an arbitrary value is set as a default value. When the threshold value is changed in the Step S13 described above, the determination is performed using the threshold value after the change. When the coefficient of variance of the body movement data acquired at the instance just passed does not reach the predetermined threshold value (No in Step S101), the controller 40 determines that the user is walking, and memorizes the magnitude of the acceleration value and the number of steps in the memory 33 together with the current day of week and time of day as the accumulated body movement data (Step S108). Therefore, the case of walking and jogging in the time zone (4), the time zone (8) in FIG. 4 and the time zone (7) in FIG. 5 correspond thereto mainly.

On the other hand, when the coefficient of variance of the body movement data acquired at the instance just passed is the predetermined threshold value or larger (Yes in Step S101), the controller 40 calculates the determination value of the body movement data acquired at the instance just passed and memorizes the same in the memory 33 (Step S102). The determination value is calculated as follows, for example. The controller 40 causes the A/D converter 35 to convert the acceleration values acquired by the accelerator sensor 31 according to the body movement of the user from analogue to digital and causes the memory 33 to memorize the acquired digital acceleration values in the memory 33 in sequence in time series, and acquires a waveform by plotting all the A/D converted values of acceleration values acquired in sequence with a lateral axis indicating the elapsed time (unit: second) and a vertical axis indicating the A/D converted value of the acceleration value (unit: count). The acquired waveform is subjected to the frequency analysis, then characteristic or representative (two, for example) frequency zones are selected, and peak-to-peak values (P-P value), average values, maximum values and minimum values in these frequency zones are calculated respectively, and at least one of these values is employed as the determination value.

Subsequently, the controller 40 determines whether or not the accumulated body movement data at the same day of week and time of day in the past corresponding to the current day of week and time of day exist (Step S103). Therefore, since no accumulated body movement data for every day of week for one week exist if at least one week is not elapsed from the start of usage, so that the determination in Step S103 is No. In the initial period of usage of the body movement detecting apparatus 10, the accumulated body movement data corresponding to the current day of week and time of day do not exist in many cases (No, in Step S12), and the determination value of the body movement data acquired at the instance just passed is memorized in the memory 33 as the accumulated body movement data together with the current day of week and time of day (time data) (Step S107).

In contrast, when at least several weeks are elapsed from the start of usage of the body movement detecting apparatus 10 and the accumulated body movement data on the same day of week and time of day in the past exist corresponding to the current day of week and time of day (Yes in Step 103), the controller 40 compares the determination value of the body movement data acquired at the instance just passed and the determination value of the accumulated body movement data (Step S104). This comparing process is performed on all the accumulated body movement data accumulated on the same day of week and time of day in the past in sequence. Consequently, the controller 40 determines whether or not there exist the accumulated body movement data having the determination values which match the determination value of the body movement data acquired at the instance just passed, or the accumulated body movement data having the determination values whose differences from the determination value of the body movement data acquired at the instance just passed fall within a predetermined range (Step S105). If it is determined not to exist (No in Step S105), the controller 40 determines that the behavior different from the accumulated body movement data on the same day of week and time of day in the past is performed, and memorizes the determination value of the body movement data acquired at the instance just passed in the memory 33 as new accumulated body movement data together with the current day of week and time of day (Step S107). In contrast, when it is determined to exist (Yes in Step S105), the controller 40 increments the number of times of matching with the matched accumulated body movement data by one, so that the number of times of matching is memorized in the memory 33 (Step S106). By storing the number of times of matching as described above, the frequencies of the respective activities of the user can be acquired as one of the accumulated body movement data.

After having performed the data accumulating process (Step 15) as described above, the controller 40 determines whether or not the body movement data acquired at the instance just passed are data in the resting state as shown in FIG. 2 (Step S16). If the body movement data acquired at the instance just passed are data determined to be No in Step S100 in FIG. 3, it can be determined to be the data in the resting state as it is (Yes in Step S16). In this case, the controller 40 determines that the energy of the resting metabolic rate is consumed from the body movement data acquired at the instance just passed, causes the computer to calculate the consumed energy by a calculation formula for the resting state, and causes the memory 33 to memorize the calculated consumed energy (Step S20) (energy computing step). As the calculation formula for the resting state, for example, "weight of user×predetermined unit time×coefficient" may be used.

When it is determined that the body movement data acquired at the instance just passed are not data in the resting state (No in Step 16), the controller 40 determines whether or not the body movement data acquired at the instance just passed are walking (Step S17). When the body movement data acquired at the instance just passed are the data determined to be No in Step S101 in FIG. 3, it may be determined to be walking as is (Yes in Step S17). In this case, the controller 40 causes the computer 32 to calculate consumed energy by a calculation formula for the walking state on the basis of the body movement data acquired at the instance just passed, and causes the memory 33 to memorize the calculated consumed energy (Step S19) (energy computing step).

When it is determined that the body movement data acquired at the instance just passed are not the walking (No in Step S17), the body movement data acquired at the instance just passed are determined to be activities other than the walking, the controller 40 causes the computer 32 to calculate the consumed energy by a calculation formula for the activities other than the walking on the basis of the body movement data acquired at the instance just passed, and memorizes the calculated consumed energy in the memory 33 (Step S18) (energy computing step).

The consumed energy per predetermined unit time calculated as in Step S18, Step S19, or Step S20 is accumulated at every predetermined unit time, and the total value is renewed as a result display on the display unit 22 (Step S21). In other words, the consumed energy in the first predetermined unit time calculated as described above is displayed as the result display on the display unit 22 as is, then the procedure goes back to Step S11. Then, the consumed energy in the second predetermined unit time is calculated, then the consumed energy in the first predetermined unit time and the consumed energy in the second predetermined unit time are added, and the display on the display unit 22 is renewed with the added total value as the result display. The consumed energy in the third predetermined unit time is also calculated, and the result display is renewed. The result display is not limited to display the consumed energy, but may include the total number of steps, the walk distance, the activity time other than the walking, the resting time, or display of data for the past several days which are counted by the controller 40.

According to the body movement detecting apparatus and the body movement detecting method in the embodiment described above, setting of the body movement detection conditions suitable for the individual user taking the activity pattern of the individual user into consideration is achieved automatically, so that accurate calculation of the consumed energy is achieved according to the body movement detected thereby.

Although the invention has been described on the basis of the above-described embodiment, the invention is not limited to the above-described embodiment, and may be improved or modified within the scope of the object of the improvement and the sprit of the invention.

INDUSTRIAL APPLICABILITY

As described thus far, the body movement detecting apparatus and the body movement detecting method according to the invention are effective when grasp of the accurate consumed energy according to the activity pattern of the individual user is necessary.

What is claimed is:

1. A body movement detecting apparatus comprising:
   a body movement data acquiring unit configured to detect a body movement of a user and acquire body movement data relating to the body movement;
   a computing unit configured to calculate consumed energy based on the body movement data;
   a time data acquiring unit configured to acquire time data, including day of week and time of day, when the body movement data are acquired;
   a data accumulating unit configured to accumulate the body movement data in correspondence with the time data; and
   a detection condition changing unit configured to change a threshold value relating to a body movement strength as a detection condition for detecting the body movement based on the body movement data and the day of week and the time of day of the time data accumulated in the data accumulating unit.

2. The body movement detecting apparatus according to claim 1, comprising:
an activity pattern data acquiring unit configured to acquire activity pattern data of the user based on the body movement data and the time data accumulated in the data accumulating unit, wherein
the detection condition changing unit is configured to change the detection condition based on the activity pattern data.

3. The body movement detecting apparatus according to claim 1, wherein:
the detection condition changing unit is configured to change the threshold value not to detect the body movement having the body movement strength which does not reach the changed threshold value.

4. The body movement detecting apparatus according to claim 1, wherein:
the threshold value is a first threshold value relating to determination whether or not the user is walking and/or running, and
the detection condition changing unit is configured to change the first threshold value so that likelihood of determination that the user is walking and/or running increases in comparison with a state before the change.

5. The body movement detecting apparatus according to claim 1, wherein a change to a power-saving mode is achieved by changing the detection condition by the detection condition changing unit.

6. The body movement detecting apparatus according to claim 1, wherein the body movement data acquiring unit is configured to acquire the body movement data at every predetermined unit time, and the detection condition changing unit is configured to change the detection condition at the every predetermined unit time.

7. The body movement detecting apparatus according to claim 1, wherein the data accumulating unit is configured to accumulate the body movement data a predetermined number of times.

8. A body movement detecting method comprising:
a body movement data acquiring step of detecting, by body movement detecting apparatus, a body movement of a user and acquiring body movement data relating to the body movement;
an energy computing step of calculating consumed energy based on the body movement data;
a time data acquiring step of acquiring time data, including day of week and time of day, when the body movement data is acquired;
a data accumulating step of accumulating the body movement data in correspondence with the time data into a memory device; and
a detection condition changing step of changing a threshold value relating to a body movement strength as a detection condition, by body movement detecting apparatus, for detecting the body movement based on the body movement data and the day of week and the time of day of the time data accumulated in the data accumulating step.

9. The body movement detecting method according to claim 8, wherein the data accumulating step accumulates the body movement data a predetermined number of times.

10. The body movement detecting method according to claim 8, wherein in the a detection condition changing step, the detection condition is changed based on the body movement data and the day of week and the time of day of the time data accumulated in the data accumulating step.

11. A body movement detecting apparatus comprising:
a body movement data acquiring unit configured to detect a body movement of a user and acquire body movement data relating to the body movement;
a computing unit configured to calculate consumed energy based on the body movement data;
a time data acquiring unit configured to acquire time data, including day of week and time of day, when the body movement data are acquired;
a data accumulating unit configured to accumulate the body movement data in correspondence with the day of week and time of day;
an activity pattern data acquiring unit configured to acquire activity pattern data including a type of the activity and a frequency of the activity taken by the user on respective days of week and respective time of day based on the body movement data and the day of week and the time of day accumulated in the data accumulating unit; and
a detection condition changing unit configured to change a threshold value relating to a body movement strength as a detection condition for detecting the body movement based on the body movement data and the activity pattern data.

* * * * *